United States Patent
Chen et al.

(10) Patent No.: US 9,427,205 B1
(45) Date of Patent: Aug. 30, 2016

(54) SYSTEMS AND METHODS FOR ARTIFACT REMOVAL FOR COMPUTED TOMOGRAPHY IMAGING

(71) Applicants: General Electric Company, Schenectady, NY (US); Wisconsin Alumni Research Foundation, Madison, WI (US)

(72) Inventors: Guang-Hong Chen, Madison, WI (US); Jiang Hsieh, Waukesha, WI (US)

(73) Assignees: General Electic Company, Schenectady, NY (US); Wisconsin Alumni Foundation, Madison, WI (US)

( * ) Notice: Subject to any disclaimer, the term of this patent is extended or adjusted under 35 U.S.C. 154(b) by 0 days.

(21) Appl. No.: 14/663,864

(22) Filed: Mar. 20, 2015

(51) Int. Cl.
  *G06K 9/00* (2006.01)
  *A61B 6/00* (2006.01)
  *A61B 6/03* (2006.01)

(52) U.S. Cl.
  CPC ............ *A61B 6/5258* (2013.01); *A61B 6/032* (2013.01)

(58) Field of Classification Search
  USPC .................................................. 382/128–134
  See application file for complete search history.

(56) References Cited

U.S. PATENT DOCUMENTS

| | | | |
|---|---|---|---|
| 4,189,775 A | 2/1980 | Inouye et al. | |
| 4,602,348 A | 7/1986 | Heat | |
| 4,751,644 A | 6/1988 | Koka et al. | |
| 4,809,172 A | 2/1989 | Hopkinson et al. | |
| 5,128,864 A | 7/1992 | Waggener et al. | |
| 5,140,520 A | 8/1992 | Matsumura | |
| 5,229,934 A | 7/1993 | Mattson et al. | |
| 5,243,664 A | 9/1993 | Tuy | |
| 5,271,055 A | 12/1993 | Hsieh et al. | |
| 5,355,310 A | 10/1994 | Brunner | |
| 5,361,291 A | 11/1994 | Toth et al. | |
| 5,400,255 A | 3/1995 | Hu | |
| 5,473,655 A | 12/1995 | Hu | |
| 5,473,656 A | 12/1995 | Hsieh et al. | |
| 5,757,951 A | 5/1998 | Tuy | |
| 6,628,744 B1 | 9/2003 | Luhta et al. | |
| 6,639,965 B1 | 10/2003 | Hsieh et al. | |
| 8,364,244 B2 | 1/2013 | Angelos et al. | |
| 2006/0120586 A1* | 6/2006 | Iatrou | A61B 6/032 382/131 |
| 2012/0170848 A1* | 7/2012 | Kemp | G06T 5/50 382/195 |

* cited by examiner

*Primary Examiner* — Alex Liew
(74) *Attorney, Agent, or Firm* — Dean D. Small; The Small Patent Law Group, LLC.

(57) ABSTRACT

An imaging system includes a computed tomography (CT) acquisition unit and at least one processor. The CT acquisition unit includes an X-ray source and a CT detector configured to collect CT imaging data of an object to be imaged. The at least one processor is operably coupled to the CT acquisition unit, and is configured to reconstruct an image using the CT imaging information; extract spatial frequency information from at least a portion of the image, wherein the spatial frequency is defined along a longitudinal direction; and remove a periodically recurring artifact from the at least a portion of the image based on a spatial frequency corresponding to a longitudinal collection periodicity to provide a corrected image.

20 Claims, 7 Drawing Sheets

SYSTEMS AND METHODS FOR ARTIFACT REMOVAL FOR COMPUTED TOMOGRAPHY IMAGING

STATEMENT REGARDING GOVERNMENT FUNDING

This invention was made with government support under EB009699 awarded by the National Institutes of Health. The government has certain rights in the invention.

BACKGROUND OF THE INVENTION

The subject matter disclosed herein relates generally to systems and methods for computed tomography (CT) imaging, for example to systems and methods for reducing periodic artifacts in CT images.

In CT imaging, an X-ray source may be rotated around an object to obtain imaging information. X-rays from the source attenuated by the object may be collected or detected by a detector and used to reconstruct an image.

In modern CT imaging, there are a number of non-ideal physical conditions that may cause artifacts in reconstructed CT images. For example, one such condition is off-focal radiation or extra-focal radiation. Off-focal radiation is caused mainly by two effects: secondary electrons and field emission electrons. The secondary electrons are typically the more dominant source. For example, when a high-speed electron beam strikes a target, electrons are again emitted from the impact area. Most of these high-velocity secondary electrons (backscatter electrons) return to the target at points outside the focal spot and produce x-ray photons at their point of impact.

Off-focal radiation may cause various problems in medical CT imaging. For example, off-focal radiation increases radiation dose to a patient. As another example, off-focal radiation may create image artifacts due to data inconsistency induced by the erroneously elevated photon counts at the detector. The impact of off-focal radiation may be dependent on the location of an object being imaged (or portion thereof) relative to the iso-ray as well as the distance to the x-ray focal spot. When off-focal radiation is present after data calibrations and data corrections, shading and blooming artifacts may appear in reconstructed images.

BRIEF DESCRIPTION OF THE INVENTION

In one embodiment, an imaging system is provided that includes a computed tomography (CT) acquisition unit and at least one processor. The CT acquisition unit includes an X-ray source and a CT detector configured to collect CT imaging data of an object to be imaged. The object includes an acquisition volume comprising a cross-section extending along a longitudinal direction. The X-ray source and CT detector are configured to be rotated relative to the object to be imaged and to collect a series of projections of the object as the X-ray source and CT detector rotate relative to the object to be imaged. The CT acquisition unit is further configured to translate axially relative to the object along the longitudinal direction to collect the CT imaging data at plural imaging locations along the longitudinal direction defining a longitudinal collection periodicity. The at least one processor is operably coupled to the CT acquisition unit, and is configured to reconstruct an image using the CT imaging information; to extract spatial frequency information from at least a portion of the image, wherein the spatial frequency is defined along the longitudinal direction; and remove a periodically recurring artifact from the at least a portion of the image based on a spatial frequency corresponding to the longitudinal collection periodicity to provide a corrected image.

In another embodiment, a method is provided that includes acquiring computed tomography (CT) imaging information of an acquisition volume comprising a cross-section extending along a longitudinal direction, wherein the CT imaging information is collected at plural imaging locations along the longitudinal direction defining a longitudinal collection periodicity. The method also includes reconstructing an image using the CT imaging information. Further, the method includes extracting spatial frequency information from at least a portion of the image, wherein the spatial frequency is defined along the longitudinal direction. Additionally, the method includes removing a periodically recurring artifact from the at least a portion of the image based on a spatial frequency corresponding to the longitudinal collection periodicity to provide a corrected image.

In another embodiment, a tangible and non-transitory computer readable medium is provided that includes one or more computer software modules configured to direct one or more processors to: acquire computed tomography (CT) imaging information of an acquisition volume comprising a cross-section extending along a longitudinal direction, wherein the CT imaging information is collected at plural imaging locations along the longitudinal direction defining a longitudinal collection periodicity, reconstruct an image using the CT imaging information; extract spatial frequency information from at least a portion of the image, wherein the spatial frequency is defined along the longitudinal direction; remove a periodically recurring artifact from the at least a portion of the image based on a spatial frequency corresponding to the longitudinal collection periodicity to provide a corrected image.

DETAILED DESCRIPTION OF THE INVENTION

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. For example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should be further understood that the figures illustrate example embodiments of the present disclosure. Variations, such as replacing or modifying one or more functional blocks, are possible to achieve similar results.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and preceded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Also used herein, the phrase "reconstructing an image" is not intended to exclude embodiments in which data representing an image is generated, but a viewable image is not. As used herein, the term "image" broadly refers to both viewable images and data representing a viewable image. It may be noted that various embodiments generate, or are configured to generate, at least one viewable image.

Various embodiments provide systems and methods for identification and/or removal of recurring artifacts (e.g., artifacts recurring along a longitudinal direction of an image caused by off-focal radiation). Various embodiments address recurring artifacts in longitudinal views (e.g., coronal, sagittal, multi-planar reformat, and/or full 3D volume) instead of in axial views, and utilize the periodic nature of the artifacts along the longitudinal direction of a CT image volume. (It may be noted that other types of artifacts may be addressed utilizing axial views in various embodiments.) For example, a periodicity may be identified based on the data acquisition parameters, with the periodicity used to identify a frequency at which recurring artifacts occur. The location of the artifacts may change based on the location of the voxel and its relative position to the x-ray source and bowtie during the data acquisition. Next, a reconstructed image may be transformed from a spatial domain to a spatial frequency domain (e.g., using FFT or other transformation methods), the artifacts identified in the spatial frequency domain image based on the identified frequency, and removed. In contrast to techniques involving calibration of imaging hardware, various embodiments provide for addressing recurring artifacts in image space, thereby reducing hardware costs and costs for calibrating hardware, as well as allowing for addressing of recurring artifacts independent of scanner type and/or scanner vendor or manufacturer. Further, while various examples are discussed herein in the context of medical imaging, it may be noted that various embodiments may be employed in flat-panel detector based cone-beam CT scanners or scanners used, for example, in security applications or pre-clinical applications.

Various embodiments provide improved imaging. A technical effect of at least one embodiment includes reduction or elimination of artifacts caused by off-focal radiation. A technical effect of at least one embodiment includes reduction or elimination of artifacts that periodically occur along a length or portion of a length of an image (e.g., along a z-axis). A technical effect of at least one embodiment includes reduction of hardware costs, for example costs associated with calibrating a system to attempt to address off-focal radiation. A technical effect of at least one embodiment includes providing elimination or reduction of recurring artifacts independent of type of scanning equipment or vendor of scanning equipment.

Figure 1:
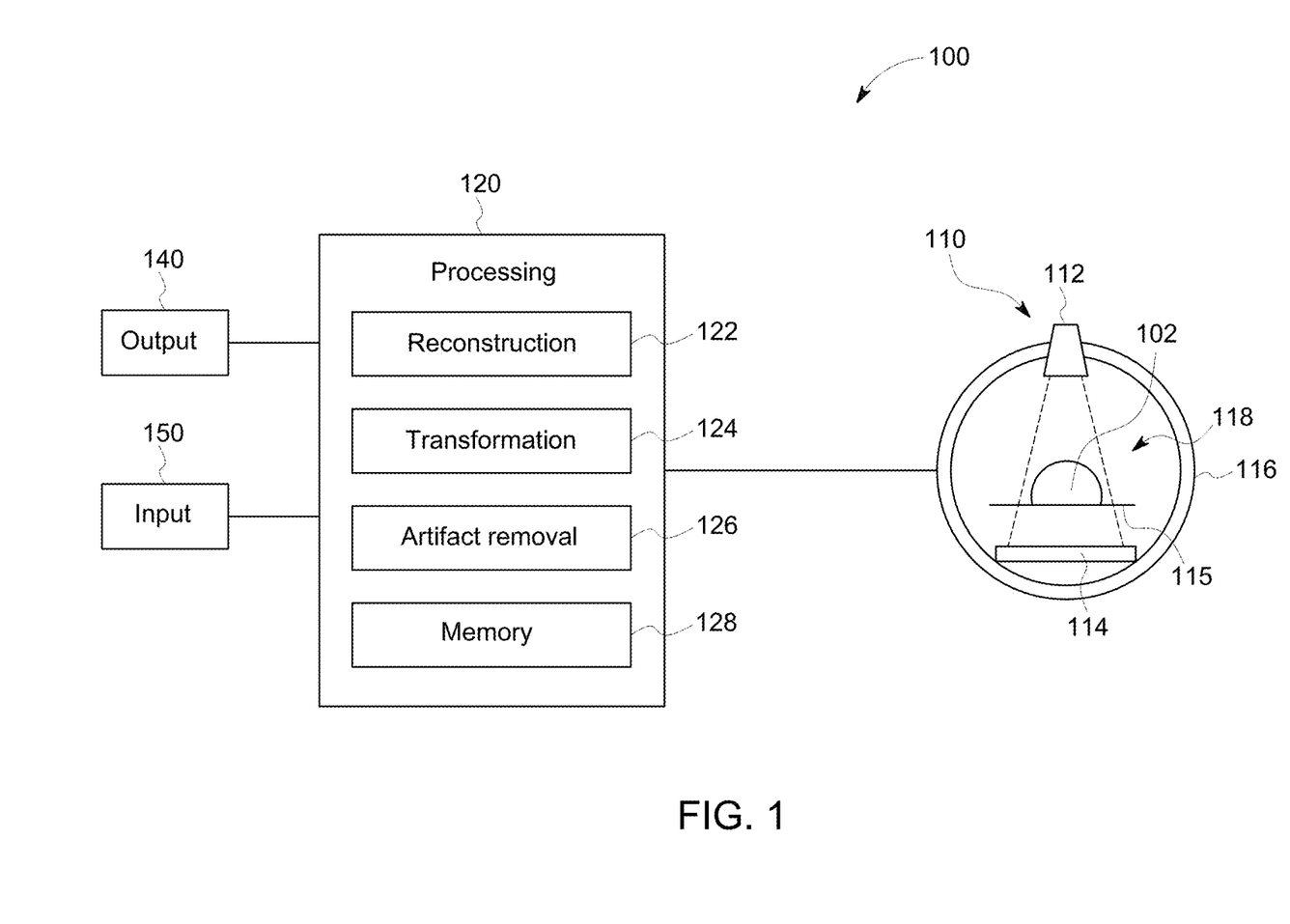
FIG. 1 is a schematic block diagram illustrating an imaging system in accordance with various embodiments.

FIG. 1 illustrates an imaging system 100 in accordance with an embodiment. The imaging system 100 may be configured, for example, to perform computed tomography (CT) scanning of an object, such as a human or animal patient (or portion thereof), such as CT scanning for a perfusion study. The imaging system 100 includes a CT acquisition unit 110 and a processing unit 120. Generally, the CT acquisition unit 110 is configured to acquire projection data or imaging data (e.g., CT data or CT imaging information), and the processing unit 120 is configured to reconstruct images using the data acquired by the CT acquisition unit 110. It may be noted that various embodiments may include additional components, or may not include all of the components shown in FIG. 1 (for example, various embodiments may provide sub-systems for use with other sub-systems to provide an imaging system). Further, it may be noted that certain aspects of the imaging system 100 shown as separate blocks in FIG. 1 may be incorporated into a single physical entity, and/or aspects shown as a single block in FIG. 1 may be shared or divided among two or more physical entities.

The depicted CT acquisition unit 110 includes an X-ray source 112 and a CT detector 114. (For additional information regarding example CT systems, see FIG. 8 and related discussion herein.) The X-ray source 112 and the CT detector 114 (along with associated components such as bowtie filters, source collimators, detector collimators, or the like (not shown in FIG. 1)) may rotate relative to the object to be imaged. For example, in some embodiments, the X-ray source 112 and the CT detector 114 may rotate about a central axis of a bore of a gantry 116 of the system 100. As another example (e.g., for small animal imaging), the X-ray source 112 and the CT detector 114 may be stationary, while the object spins or rotates about a fixed axis.

Generally, X-rays from the X-ray source 112 may be guided to an object 102 to be imaged through a source collimator and bowtie filter. The object 102 to be imaged, for example, may be a human patient, or a portion thereof (e.g., head or torso, among others). The source collimator may be configured to allow X-rays within a desired field of view (FOV) to pass through to the object to be imaged while blocking other X-rays. The bowtie filter may be configured to absorb radiation from the X-ray source 112 to control distribution of X-rays passed to the object to be imaged.

X-rays that pass through the object to be imaged are attenuated by the object 102 and received by the CT detector 114 (which may have a detector collimator associated therewith), which detects the attenuated X-rays and provides imaging information to the processing unit 120. The processing unit 120 may then reconstruct an image of the scanned portion of the object 102 using the imaging information (or projection information) provided by the CT detector 114. The processing unit 120 may include or be operably coupled to the output unit 140, which in the illustrated embodiment is configured to display an image, for example, an image reconstructed by the processing unit 120 using imaging information from the CT detector 114. The depicted input unit 150 is configured to obtain input corresponding to a scan to be performed, with the processing unit 120 using the input to determine one or more scan settings (e.g., tube voltage, tube current, scanning rotation speed, or the like). The input unit 150 may include a keyboard, mouse, touchscreen or the like to receive input from an operator, and/or may include a port or other connectivity device to receive input from a computer or other source.

In the illustrated embodiment, the X-ray source 112 is configured to rotate about the object 102. For example, the X-ray source 112 and the CT detector 114 may be positioned about a bore 118 of the gantry 116 and rotated about the object 102 to be imaged. As the X-ray source 112 rotates about the object 102 during an imaging scan, X-rays received by the CT detector 114 during one complete rotation provide a 360 degree view of X-rays that have passed through the object. Other imaging scanning ranges may be used in alternative embodiments. The CT imaging information may be collected as a series of views that together make up a rotation or portion thereof. Each view or projection may have a view duration during which information (e.g., counts) is collected for the particular view. The view duration for a particular view defines a CT information acquisition period for that particular view. For example, each rotation may be made up of about 1000 views or projections, with each view or projection having a duration or length of about 1/1000 of a complete rotation. The X-ray source may be turned on and off to control the acquisition time. For example, to perform an imaging scan of a complete rotation, the X-ray source may be turned on at a particular rotational position of the gantry and turned off when the X-ray source returns to the particular rotational position after a complete rotation.

Figure 2:
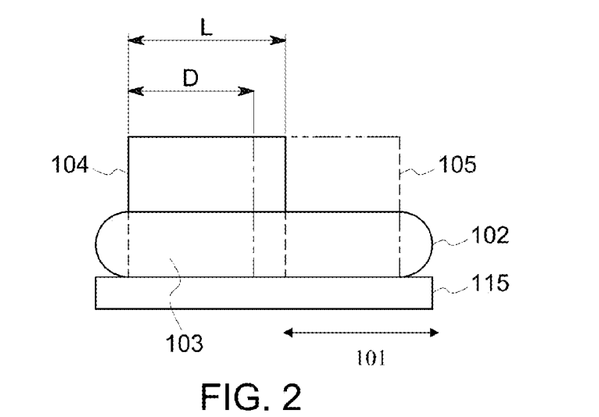
FIG. 2 illustrates a side view of the imaging system of FIG. 1.

The imaging system 100 may be configured to acquire or collect CT information at plural imaging locations along a longitudinal direction. The imaging locations may be continuous (e.g., in a helical scan where a table or bed moves longitudinally with respect to one or more detectors during rotation) or discrete (e.g., in a step and shoot technique in which the table or bed does not move longitudinally with respect to one or more detectors during rotation, but instead is articulated longitudinally by a step or increment between rotations or information collection). FIG. 2 depicts a side view of the object 102 being imaged using the imaging system 100 of FIG. 1. As seen in FIG. 2, the object 102 is supported by a table or bed 115. As the X-ray source 112 and CT detector 114 (not shown in FIG. 2 for ease and clarity of illustration) translate axially along a longitudinal direction 101 with respect to the object 102, imaging information is collected at multiple imaging locations. In the depicted example, two imaging locations are shown, namely a first imaging location 104 and a second imaging location 105. The respective volumes defined by the first imaging location 104 and the second imaging location 105 define an acquisition volume 103.

The acquisition volume 103 may be understood as being defined by the cross-section of the object 102 (e.g., the shape of the object in an x-y plane where the longitudinal direction 101 is denoted as a z-direction) extending along the longitudinal direction 101. For example, in a step and shoot mode of operation, the X-ray source 112 and the CT detector 114 may be rotated about the object 102 while remaining stationary with respect to the object 102 along the longitudinal direction 101, collecting imaging information during a rotation over the length L. The length L in the illustrated embodiment is defined by the detector coverage along the length at the iso-center (e.g., the center of rotation) of the imaging system 100. After a desired amount of information is collected (e.g., a complete rotation), the X-ray source 112 and CT detector 114 may be advanced an increment (or step) D to collect additional imaging information at the second imaging location 105. It may be noted that the increment D in the illustrated embodiment is less than the length L, resulting in an overlap between the information collected at the first imaging location 104 and the second imaging location 105. In alternate embodiments, the increment D may be equal to L, resulting in no overlap between the information collected at the first imaging location 104 and the second imaging location 105. As another example, in a helical mode of operation, the X-ray source 112 and the CT detector 114 may be rotated about the object 102 while also translating longitudinally with respect to the object 102 along the longitudinal direction 101. The distance D may then be understood as the longitudinal distance translated between corresponding rotational locations of the X-ray source (e.g., the distance traveled during one rotation, for example, from a 12:00 rotational position of the X-ray source to the next 12:00 rotational position of the X-ray source). It may be noted the relative longitudinal movement of the table may be achieved by moving an X-ray source and detector while maintaining the table in a stationary longitudinal position, moving the table while maintaining the X-ray source and detector in a stationary longitudinal position, or moving both the table and the X-ray source and detector (e.g., at different speeds and/or in different directions relative to each other).

Figure 3:
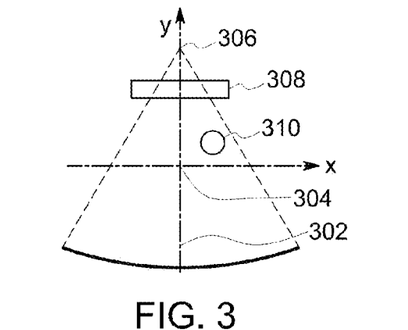
FIG. 3 illustrates an object located at a distance from an iso-center.

Off-focal radiation or extra-focal radiation, among other sources, may cause artifacts in CT images. The impact of off-focal radiation artifacts is heavily dependent on the image object's location (or location of one or more portions thereof) relative to the iso-ray as well as the distance of the image object (or one or more portions thereof) to the x-ray focal spot. The impact of off-focal radiation artifacts is also heavily dependent on the x-ray source position relative to the location of the object being imaged (or the location of one or more portions thereof). FIG. 3 depicts a portion of an object that is disposed at a distance to an iso-ray and a distance to the x-ray source. As seen in FIG. 3, the iso-ray 302 passes through the iso-center 304 (or center of rotation) and the focal spot 306. The object 310 is disposed at a distance from the iso-ray 302. The disposed distance changes with the x-ray source position (in the illustrated embodiment, the source is at a 12 o'clock position). Therefore, during the data acquisition, the x-ray photons passing through the object 310 pass through different portions of the bowtie filter 308. For example, the object 310 may be an arm of a patient being imaged, with the patient positioned so that the iso-center is disposed within an envelope defined by the torso. Thus, over the rotation of the x-ray source having focal spot 306, the object 310 is at different distances from the iso-ray 302 (and bowtie filter) and the impact of off-focal radiation also changes. Off-focal radiation may result, for example, in shading or blooming artifacts appearing in reconstructed images.

Figure 4:
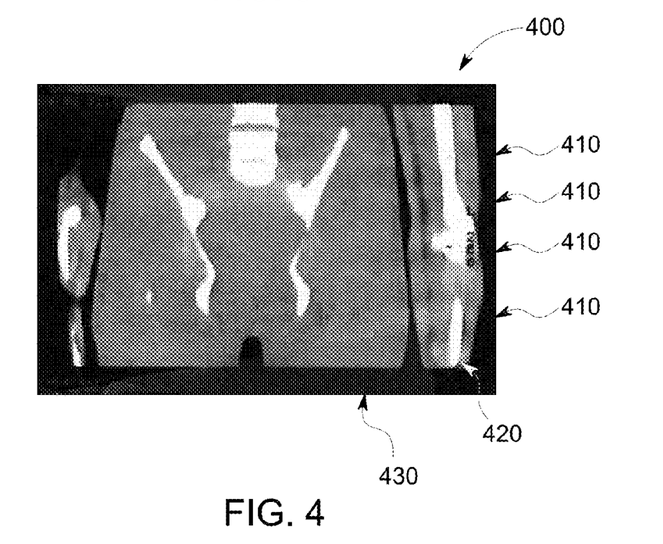
FIG. 4 illustrates periodically recurring artifacts.

The artifacts may appear as bands extending across a portion of an image, for example as seen in FIG. 4. FIG. 4 illustrates an image 400 of a phantom in a coronal (x-z plane) showing bands 410 occurring near an arm 420 in the image, as well as toward an exterior edge of a torso 430 of the image. The bands 410 in the illustrated image 400 are generally darker in color than the surrounding image, and are more prevalent toward the edge, or away from the center of the image 400. The repeating nature of the bands 410 may result from the collection of imaging information at plural locations along the length of the object being imaged, resulting in an artifact (or artifacts) that repeats at different positions along the length of the image 400. The repetition may correspond to a longitudinal collection periodicity defined along the length of the object being imaged based on the axial or longitudinal translation of the X-ray source and CT detector relative to the object.

In various embodiments, the periodic or repeating nature of the artifacts is advantageously analyzed to identify and reduce or remove the artifacts from an image. For example, in various embodiments, the periodic nature of the artifacts may result in identifiable locations along a power spectrum of an image (e.g., a spectrum over a range of spatial frequencies over the length of the image). Spatial frequencies or ranges of frequencies corresponding to artifacts may be identified based on the longitudinal collection periodicity of the collected imaging information and/or the image. For example, for imaging information collected in a step and shoot mode, the longitudinal collection periodicity may be defined as the step or increment between imaging locations. As another example, for imaging information collected in a helical mode, the longitudinal collection periodicity may be defined as $T = L \times K$, where T is the periodicity, L is the detector coverage along the length at the iso-center, and K is the helical pitch. By way of example, a 64-slice CT scanner may be employed in a helical mode having an L of 40 millimeters and K within range between 0.5 and 1.5. In either case, the locations of artifacts in spatial frequency space are related to the characteristic spatial frequency defined by the inverse of the periodicity of the artifacts.

Generally, the processing unit 120 in various embodiments identifies artifacts based on the periodicity. For example, with an image transformed into a spatial frequency domain image, the processing unit 120 may identify artifacts based on peaks located at a spatial frequency corresponding to the periodicity. For example, the spatial frequency at which artifacts are identified (and removed) may be defined as the inverse of the periodicity, may be a range that includes the inverse of the periodicity, or may be a value near the periodicity (for example, the frequency may be adjusted based on an observed peak or peaks near the inverse of the periodicity to determine and/or account for any differences between the artifact frequency for a system in use and a theoretical or otherwise predetermined or estimated artifact frequency (e.g., based on a nominal periodicity)).

The processing unit 120, in various embodiments, acquires CT imaging information from the acquisition unit 110 and reconstructs an initial image using the CT imaging information. For example, the CT imaging information may be acquired in projection space and transformed into a reconstructed image in image space. The processing unit 120 may next transform at least a portion of the reconstructed image to a spatial frequency domain (defined along the longitudinal direction) to provide a spatial frequency domain image. By way of example, the selection of the portion of the image may be performed based on a scout image, or, as another example, may be performed in an iterative fashion. For the iterative fashion, a portion of the reconstructed image with length R may first be selected and an artifact signature obtained from the spatial frequency image. R may then be changed to a different value and the above process repeated. Further, the image portion may also be shifted along the longitudinal direction (z-axis), and the process repeated. After several iterations, the size and location corresponding to the maximum "artifact signature" may be identified and used for the artifact removal process. It may be noted that the entire image volume may be used to conduct the artifact analysis. To minimize the impact of image noise on the artifact identification, iterative reconstruction or image spacing smoothing may be performed in various embodiments prior to the artifact identification step. Next, the processing unit 120 may remove a periodically recurring artifact from the spatial frequency domain image based on a spatial frequency corresponding to the longitudinal collection periodicity to provide a corrected spatial frequency domain image. After removing the periodically recurring artifact from the spatial frequency domain image, the processing unit 120 may perform an inverse transform on the corrected spatial frequency domain image to provide a corrected image in a spatial domain of image space. It may be noted that the artifact identification and removal may be performed in an image domain (e.g., via use of a correlation to map an object image with an artifact pattern generated based on the acquisition parameters). The advantages of such an approach include added flexibility since the correlation calculation can be performed at various sizes and locations; however, such an approach may have disadvantages with respect to computational efficiency. It may be noted that a mixed mode of operation can also be performed in which at least one iteration of artifact removal is performed in a frequency domain and at least one iteration of artifact removal is performed in an image domain. The artifact identification and removal may be addressed independently of scanner type and/or vendor of scanner.

It may be noted that, in some circumstances, it may be possible that anatomical structures may have a spatial frequency at or near the spatial frequency corresponding to the longitudinal collection periodicity (referred to herein as the longitudinal collection frequency) or the spatial frequency of recurring artifacts due to off-focal radiation. Generally, the anatomical structures most likely to have spatial frequencies in the general range of the frequency corresponding to the longitudinal collection frequency are bony structures, such as ribs. Accordingly, before a spectral analysis or other identification of one or more recurring artifacts, a reconstructed image may first be segmented into a soft tissue segmented image and a bony structure (or other high density structure or very low density structure) segmented image. It may be noted that, in various embodiments, the intensity of the recurring artifacts is generally low (e.g., less than 100 Houndsfield Units (HU)). Accordingly, a threshold may be used to identify regions of a reconstructed image that include soft tissue, and segment the image into separate images of soft tissue and bony structure. For example, any pixels that fall in a range of ($f_{min}$, $f_{max}$) are classified as soft tissue. By way of example for illustrative purposes, $f_{min}$ may be set at −500 HU and $f_{max}$ at 200 HU. Bony and air regions of the soft tissue segmented image may be filled with a nominal tissue value of 0 HU. Then, the soft tissue segmented image (and not the bony structure segmented image) may be transformed into a spatial frequency domain and examined or analyzed for the presence of recurring artifacts and the removal of the recurring artifacts. Further, after the soft tissue segmented image is processed to provide a corrected image (e.g., transformed to a spatial frequency domain, analyzed for removal of recurring artifacts, and inverse transformed from the spatial frequency domain), the corrected image (e.g., the corrected soft tissue image) may be combined with the bony structure segmented image to provide a combined corrected image.

In various embodiments, a spectral analysis may be performed along the length of an object being imaged (or along the longitudinal direction 101) to identify and/or remove artifacts that recur at or near a frequency corresponding to the longitudinal collection periodicity. For example, if a reconstructed image volume (e.g., a complete image volume, or, as another example, a segmented image volume corresponding to soft tissue) is denoted as p(x, y, z), where z is the longitudinal direction, a spectral analysis may be performed along the z direction. The spectral analysis may be carried out, for example, using a Fourier transform, wavelet transform, or the like. The output of the spectral analysis in various embodiments may be a spatial frequency domain image, which corresponds to or is represented by a three-dimensional function S(x, y, ω), where ω is a frequency variable corresponding to a longitudinal frequency, or frequency in the z-direction. In various embodiments, recurring artifacts may not change sharply in the x-y plane. Accordingly, noise may be removed (e.g., by the processing unit 120) utilizing a low-pass filter applied to S(x, y, ω) before analyzing S(x, y, ω) for recurring artifacts.

A thresholding analysis may then be used to eliminate artifactual power in the power spectrum. For example, the particular threshold value (or values) may be determined adaptively based on global characteristics of an imaging volume, or based on local statistics. Generally, the threshold value or values may be set so that values attributable to the recurring artifact are removed using the threshold while values attributable to soft tissue in the absence of the recurring artifact are retained to the extent possible or practical.

In some embodiments, the periodically recurring artifact may be removed via a thresholding analysis performed across at least one of a coronal or a sagittal plane. For example, for performance across a coronal plane, a line may be defined through a spatial frequency image corresponding to a constant value of x (or range of constant x values). The line may be examined for any peaks satisfying or exceeding a threshold at a frequency or range of frequencies corresponding to the longitudinal collection periodicity. If any peaks or values are located along the line satisfying or exceeding the threshold, those values may be removed. After one line is examined, the next or adjacent line (e.g., moving in a left-to-right direction) may be examined, until all lines have been examined. Alternatively or additionally, a thresholding analysis may be performed along a sagittal plane (or front-to-back). After recurring artifacts have been removed, any resulting holes or un-defined portions of an image may be filled in, for example, using interpolation from surrounding structures.

It may be noted that recurring artifacts (e.g., artifacts that recur along a length of an image) may not be readily discernible in axial views; however, due to the physical causes of the recurring artifacts (e.g., off-focal radiation that repeats at different collection positions along the length of the object), the artifacts may present a periodic structure in views in an x-z (coronal) or y-z (sagittal) plane. Further, while bands or other recurring artifacts may appear as "non-local" (e.g., as not being limited to a single discrete location, or as being spread out or distributed in different locations) in a spatial domain, recurring artifacts may be localized (e.g., to a frequency of interest or range of frequencies corresponding to a longitudinal collection periodicity), allowing for removal of the artifact while still preserving background anatomy. Accordingly, as discussed herein, in various embodiments, imaging information in image space may be transformed from a spatial domain to a frequency domain, recurring artifacts removed in the frequency domain to provide a corrected frequency domain image, and the corrected frequency domain image may be transformed into the spatial domain.

It may further be noted, however, that, due to the complexity of scanning systems as well as objects being scanned, recurring artifacts may deviate from predicted or expected frequency. Accordingly, in some embodiments, a theoretical or otherwise predetermined frequency corresponding to a longitudinal collection periodicity (e.g., a frequency that is the inverse of the longitudinal collection periodicity) may be adjusted or modified to account for or address any deviations. For example, peaks observed within a range of an expected frequency may be identified as recurring artifacts.

Artifact removal may be achieved via a first step of band detection and a second step of band rectification. In some embodiments, the processing unit 120 may be configured to identify a periodically recurring artifact (e.g., employing a spectral analysis of at least a portion of a reconstructed image), generate a standardized periodic structure corresponding to the identified periodically recurring artifact to provide a rectified image, and remove the periodically recurring artifact from the rectified image to provide a corrected spatial frequency domain image. Providing a rectified image as discussed herein helps to equalize the artifact intensities across the entire image volume. Generally, the intensity of an image artifact tends to appear to be stronger near the periphery of a patient relative to the center of the patient. Therefore, rectification in various embodiments aids in the identification of image artifacts. For example, a rectification mask may be generated based on an identified periodically recurring artifact, and the rectification mask may be applied to a spatial frequency domain image to provide the rectified image. The rectification mask may be generated using a reference or coach image depicting an expected or predetermined recurring artifact modified or adjusted based on identified peaks in a spatial frequency domain image.

In another embodiment, an artifact identification and removal process is carried out in a preferred orientation (e.g., sagittal or coronal plane) based on the patient orientation (e.g., supine or side). Patient orientation information can be obtained from either a priori information (e.g., scan protocol) or based on scout image.

In yet another embodiment, artifact identification and removal process is carried out iteratively in multiple orientations. For example, the processing can be first performed in sagittal plane followed by coronal plane. Such processes can be repeated multiple times until predetermined criteria are met.

In yet another embodiment, location information can be incorporated into the artifact detection and correction. For example, generally, artifact intensity is higher near the periphery of a patient than the center of the patient. Therefore, the threshold and strength of the correction can be adjusted based on the location of the region relative to the object boundary. Further, artifacts typically appear stronger corresponding to steeper slopes of a bowtie filter. Therefore, such information can be incorporated in the artifact identification and correction steps.

Figure 6A:
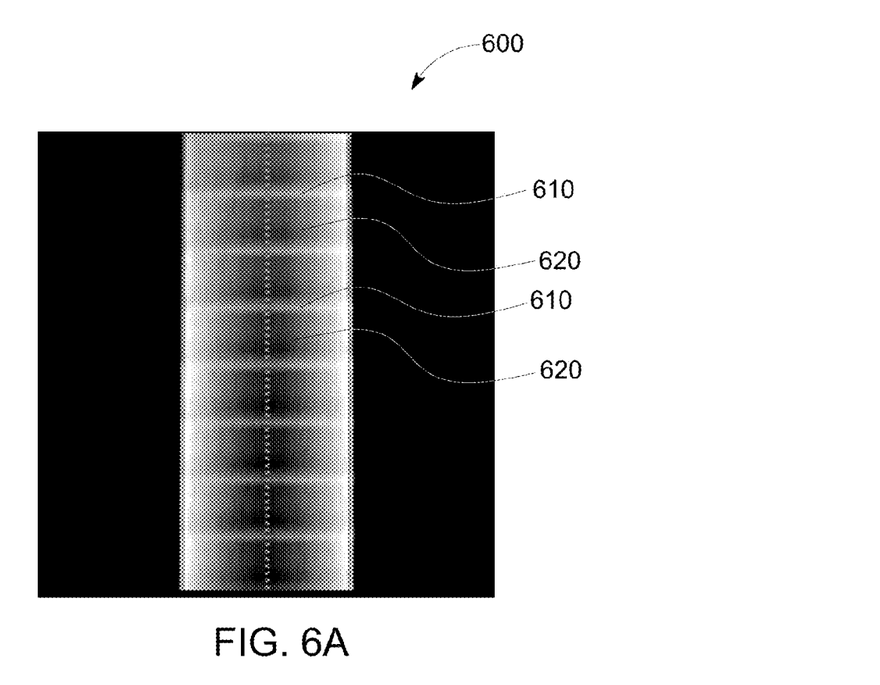
FIG. 6A is a reference image for bands for a step and shoot mode of imaging information collection in accordance with various embodiments.

For example, FIG. 6A depicts a reference image 600 for use in conjunction with a step and shoot mode of acquisition. The reference image 600 includes light bands 610 and dark bands 620 spaced at a periodically recurring interval corresponding to the longitudinal collection periodicity. For example, the recurring bands of the reference image 600 may be based on a mathematical calculation of the periodicity based on physical parameters of the imaging system (e.g., the length of the increment or step between collection locations), and/or based on physical tests or calibrations of an imaging system. As seen in FIG. 6A, the bands of the reference image 600 extend across the reference image 600, and represent theoretical bands (light and dark) extending across an image due to a measured or otherwise determined or calculated longitudinal collection periodicity. Based on acquired imaging information, the reference image 600 may be adjusted to more closely match actually experienced peak frequencies for a given acquired image to provide a rectification mask, and then applied to a reconstructed image to provide a rectified image. While actual peaks may have a different shape, in the standardized model the rectified periodic artifacts may be represented using a Gaussian distribution.

Figure 6B:
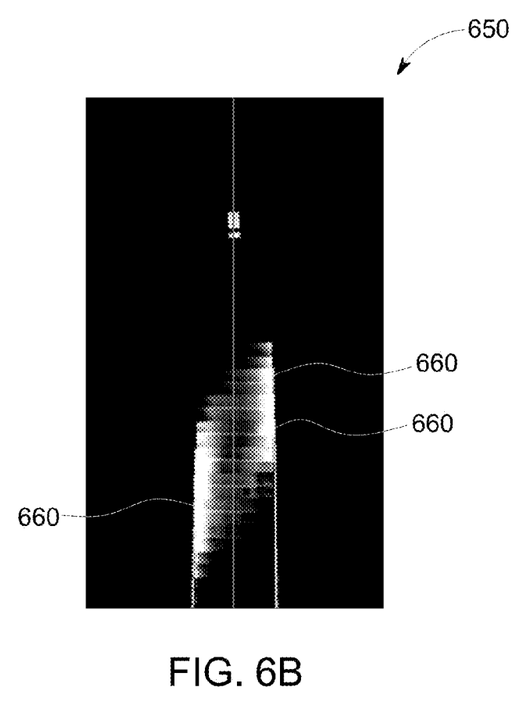
FIG. 6B is a reference image for bands for a helical mode of imaging information collection in accordance with various embodiments.

FIG. 6B depicts a reference image 650 for use in conjunction with a helical mode of acquisition. In the reference image 650, some of the bands 660 extend across a depicted object, while other bands 660 do not. Further, the bands 660 tend to be brighter away from the center of the image 650, or toward the edge.

Figure 7:
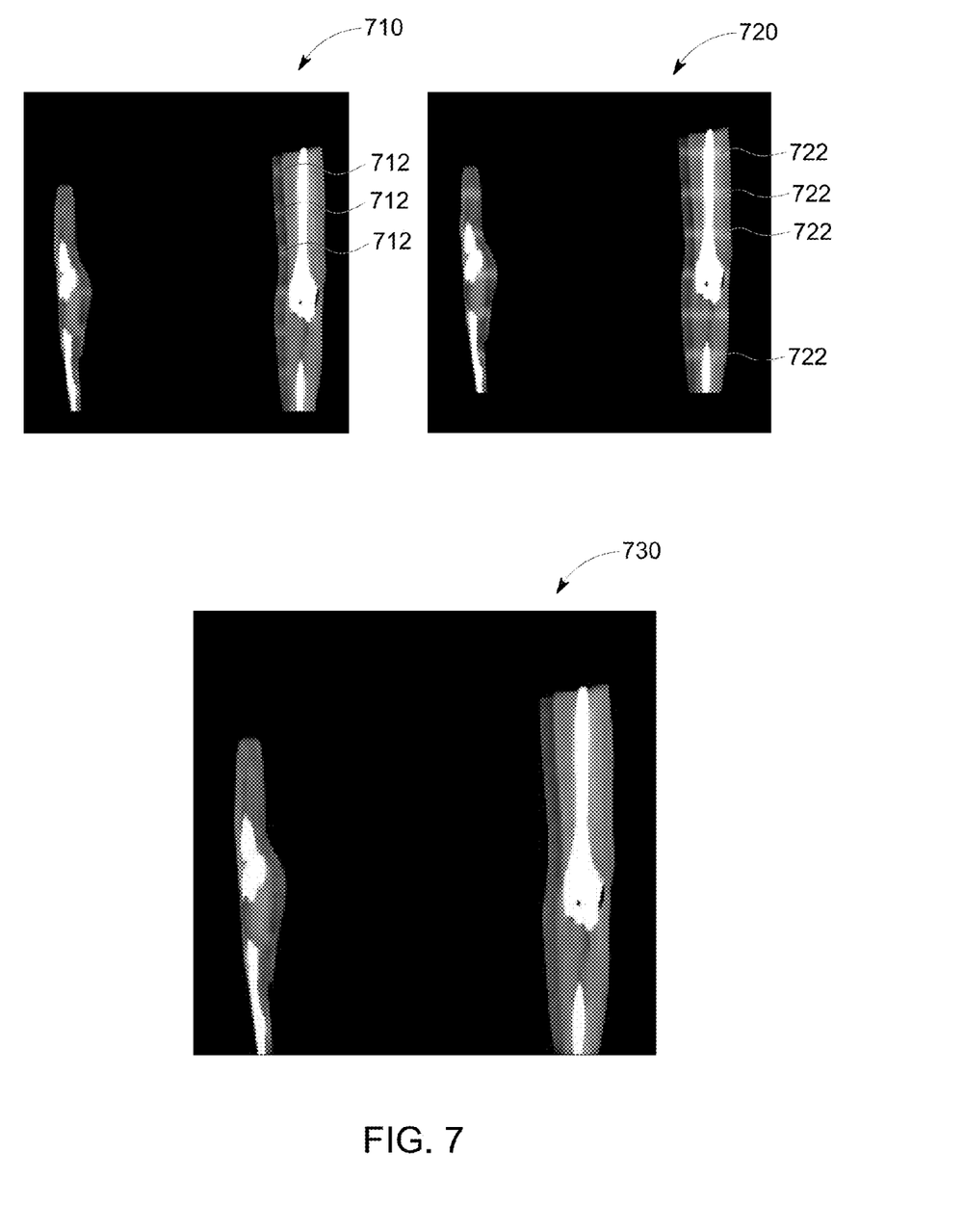
FIG. 7 depicts an original image, a rectified image, and a corrected image in accordance with various embodiments.

Generally, the reference image (600 or 650) may be adjusted based on detected peaks to generate a rectification mask, which may be applied to an image to provide a rectified image. FIG. 7 depicts an example original image 710, rectified image 720, and a processed or corrected image 730. As seen in FIG. 7, the original image 710 includes bands 712 due to recurring artifacts that are located primarily near an edge of an imaged object. The rectified image 720 includes standardized bands 722 extending generally across the rectified image 720, and, after removal of the artifacts, the corrected image 730 has the bands removed or reduced. After removal of the artifact, portions of the image from which the artifact has been removed may be filled in, for example, using interpolation from surrounding tissue represented in the image. It may be noted that different types of bands (e.g., dark and light) may be separately detected and removed, and/or a given type of band may be removed iteratively (e.g., an initial portion of the band removed, further detection or analysis performed to determine if any remaining band exceeds a level of acceptability, and further removal of an additional portion or portions of the band as appropriate). It may be noted that images of FIG. 7 are depicted in a spatial domain for ease of illustration; however, it may be noted that the artifacts may be identified and removed using frequency domain images.

As indicated herein, the processing unit 120 is configured to control various aspects of the acquisition unit and/or to reconstruct an image using information obtained via the acquisition units. For example, the processing unit 120 may be configured to reconstruct a CT image using information collected by the CT acquisition unit 110.

The depicted processing unit 120 is operably coupled to the input unit 150, the output unit 140, and the CT acquisition unit 110. The processing unit 120, for example, may receive imaging data or projection data from the CT detector 114. As one more example, the processing unit 120 may provide control signals to one or more aspects of the CT acquisition unit 110, such as the X-ray source 112 and CT detector 114. In various embodiments, the processing unit 120 includes processing circuitry configured to perform one or more tasks, functions, or steps discussed herein. It may be noted that "processing unit" as used herein is not intended to necessarily be limited to a single processor or computer. For example, the processing unit 120 may include multiple processors and/or computers, which may be integrated in a common housing or unit, or which may be distributed among various units or housings. It may be noted that operations performed by the processing unit 120 (e.g., operations corresponding to process flows or methods discussed herein, or aspects thereof) may be sufficiently complex that the operations may not be performed by a human being within a reasonable time period. For example, the reconstruction of an image, the segmentation of an image, the transforming of an image into a frequency domain, the spectral analysis of a frequency domain image, the removal of artifacts, or the performing of an inverse transform on a frequency domain image may rely on or utilize computations that may not be completed by a person within a reasonable time period.

The depicted processing unit 120 is configured to control the CT acquisition unit 110 (e.g., by controlling the activation and deactivation of the X-ray source 112) to collect CT information for reference projections and sample projections, as well as to collect CT imaging information during an imaging scan. The processing unit 120 may also control a longitudinal translation of the CT acquisition unit 110 relative to the object being imaged. For example, the processing unit 120 may control the CT acquisition unit to advance a given distance along the length of an object being imaged as a step or increment between rotations, and may use the length to determine a periodicity and/or a corresponding frequency to be used in conjunction with identifying or removing periodic artifacts.

In the illustrated embodiment, the processing unit includes a reconstruction module 122, a transformation module 124, an artifact removal module 126, and a memory 128. It may be noted that other types, numbers, or combinations of modules may be employed in alternate embodiments, and/or various aspects of modules described herein may be utilized in connection with different modules additionally or alternatively. Generally, the various aspects of the processing unit 120 act individually or cooperatively with other aspects to perform one or more aspects of the methods, steps, or processes discussed herein.

The depicted reconstruction module 122 is configured to reconstruct one or more images using imaging or projection data acquired from the CT detector 114. For example, the reconstruction module 122 may receive imaging information from the CT detector 114 taken over a number of views (e.g., for a full rotation or portion thereof, or for a number of rotations taken at different positions along the length of an object to be imaged) and reconstruct an image used for diagnostic purposes. The reconstruction module 122 may also, in various embodiments, segment a reconstructed image (e.g., into a bony structure segmented image and a soft tissue segmented image) and/or combine previously segmented images into a combined image.

In the illustrated embodiment, the transformation module 124 is configured to receive an image (or portion thereof such as a soft tissue segmented image) in a spatial domain from the reconstruction module 122, and to transform the image (or portion thereof), while still in image space (in contrast to projection or sinogram space) to a spatial frequency domain, where the frequency corresponds to a length of an imaged object. For example, in various embodiments, a Fourier transform or wavelet transform may be utilized to transform an image from a spatial domain to a frequency domain. Additionally, the transformation module 124 may receive a corrected image in a spatial frequency domain from the artifact removal module 126, and transform the corrected image from the spatial frequency domain to a spatial domain.

With continued reference to FIG. 1, the depicted artifact removal module 126 is configured to receive a spatial frequency image from the transformation module, and to identify and/or remove a recurring artifact from the spatial frequency image to provide a corrected spatial frequency image. For example, as discussed herein, the artifact removal module 126 may perform a thresholding analysis (e.g., performed across at least one of a coronal plane or a sagittal plane) to remove recurring artifacts. As another example, as also discussed herein, the artifact removal module 126 may identify a recurring artifact, generate a rectified image based on the detected recurring artifact, and then remove the artifact from the rectified image. The artifact removal module 126 (and/or other aspect of the processing unit 120) may also be configured to fill in portions of the image left undefined after artifact removal (e.g., using interpolation based on surrounding tissue) and/or to perform noise removal on an image or portion thereof.

The memory 128 may include one or more computer readable storage media. The memory 128, for example, may store system parameters from which a periodicity may be determined, image data corresponding to images generated, results of intermediate processing steps, or the like. Further, the process flows and/or flowcharts discussed herein (or aspects thereof) may represent one or more sets of instructions that are stored in the memory 128 for direction of operations of the system 100.

The output unit 140 is configured to provide information to a user. The output unit 140 may be configured to display, for example, information regarding a detected recurring artifact, or, as another example, one or more images using information obtained during one or more corresponding imaging scans. The output unit 140 may include one or more of a screen, a touchscreen, a printer, or the like.

The input unit 150 may be configured to obtain an input that corresponds to one or more settings or characteristics of a scan to be performed, and to provide the input (or information corresponding to the input) to the processing unit 120, which may use the input to determine, adjust, or select parameters used for performing a scan (e.g., amount of rotation, increment of longitudinal step between rotations, number of increments or steps, helical pitch, or the like). The input unit 150 may be configured to accept a manual user input, such as via a touchscreen, keyboard, mouse, or the like. Additionally or alternatively, the input unit 150 may receive information from another aspect of the imaging system 100, another system, or a remote computer, for example, via a port or other connectivity device.

Figure 5A:
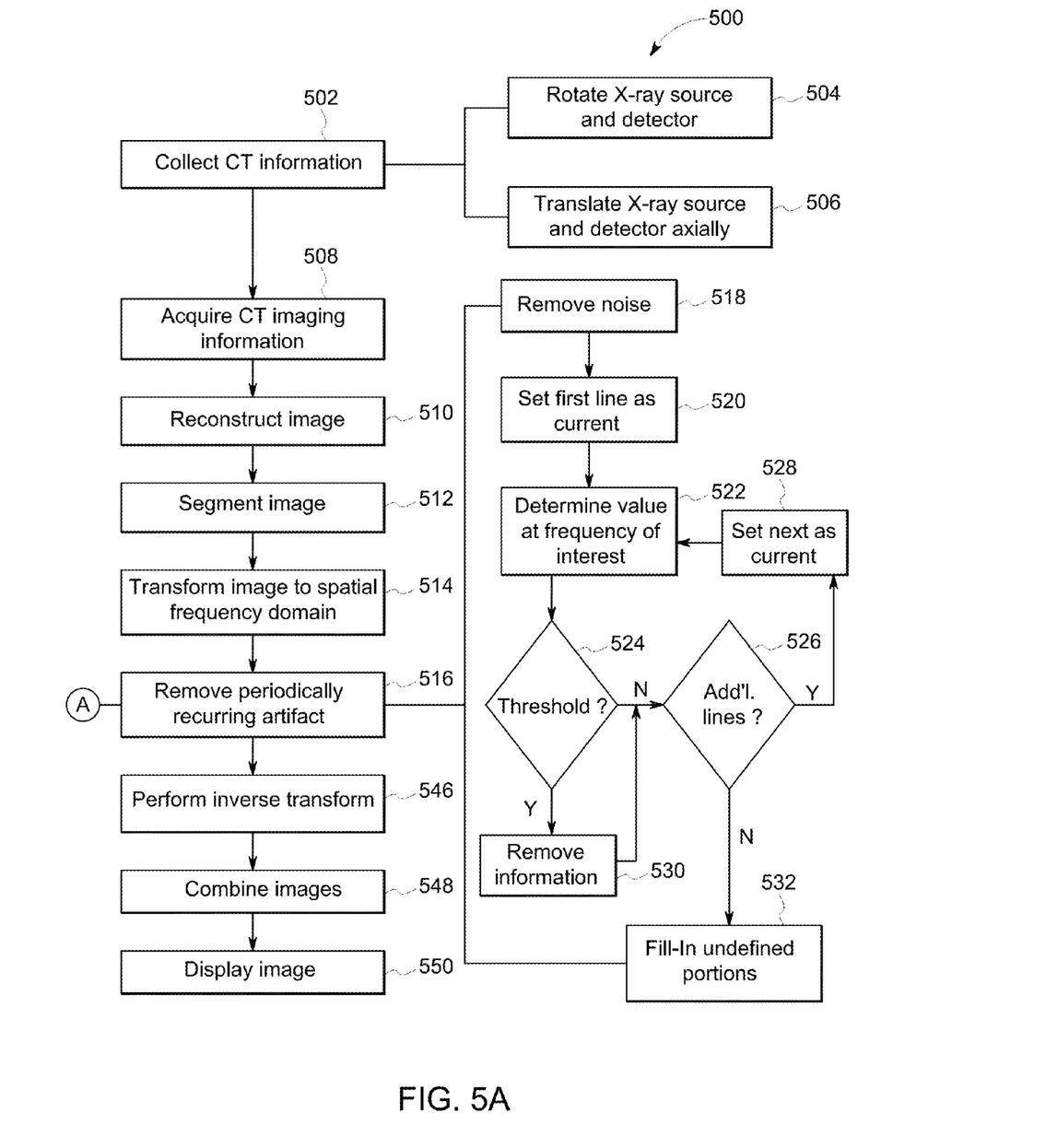
FIG. 5A is a flowchart of a method in accordance with various embodiments.
Figure 5B:
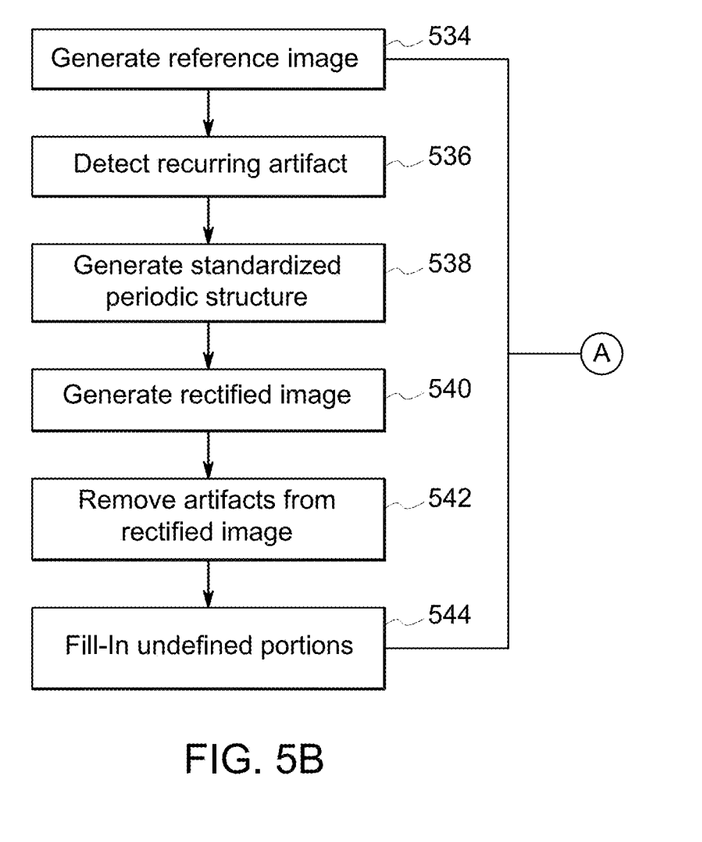
FIG. 5B is an additional portion of the flowchart of FIG. 5A.

FIGS. 5A and 5B provide a flowchart of a method 500 for imaging an object, for example as part of a perfusion study, in accordance with various embodiments. The method 500, for example, may employ or be performed by structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 500 may be able to be used as one or more algorithms to direct hardware (e.g., one or more aspects of the processing unit 120) to perform one or more operations described herein. It may be noted that, in the illustrated embodiment, a transformation to a spatial frequency domain is used to identify and remove periodically recurring artifacts. In other embodiments, other techniques may be employed additionally or alternatively.

At 502, CT information is collected (e.g., using an acquisition unit such as acquisition unit 110). The CT information may be collected by rotating an x-ray source and detector relative to an object to be imaged at 504, as well as by translating the x-ray source and detector axially or longitudinally relative to the object to be imaged at 506. The axial or longitudinal translation may occur at the same time as the rotation in some embodiments (e.g., during a helical mode of operation), or may occur in steps or increments between rotations (e.g., during a step and shoot mode of operation). The axial or longitudinal translation may occur at a longitudinal collection periodicity corresponding to distance traveled between rotations, or between similar rotational orientations of the acquisition unit. For example, for a step and shoot mode of operation, the longitudinal collection periodicity may be defined as the step or increment between imaging locations. As another example, for imaging information collected in a helical mode, the longitudinal collection periodicity may be defined as $T = L \times K$, where T is the periodicity, L is the detector coverage along the length at the iso-center, and K is the helical pitch.

At 508, CT imaging information (e.g., the information collected at 502) is acquired, for example of an acquisition volume of an object. The CT imaging information in various embodiments is information that has been acquired at plural imaging locations along a longitudinal direction. In some embodiments, the CT imaging information may be acquired by one or more processors directly from an acquisition unit. In some embodiments, the CT imaging information may be acquired from a storage device, memory device, and/or network or internet connection. The one or more processors that acquire the CT imaging information may be integral with an acquisition unit as part of an imaging system located at a single location, or the one or more processors may be located remotely from the acquisition unit.

At 510, an image is reconstructed using the CT imaging information. For example, the CT imaging information may be acquired in projection or sinogram space, and the image reconstructed in image space. The reconstructed image may be, for example, in a spatial domain of image space, and represented by a function p(x, y, z), where z is a longitudinal direction, an x-z plane is a coronal plane, a y-z plane is a sagittal plane, and an x-y plane is an axial plane (e.g., a plane oriented normal to an axis passing along the length of an object being imaged). Longitudinally recurring artifacts may be most readily visible and/or identifiable in the coronal plane and/or sagittal plane.

At 512, the image is segmented. For example, the image may be segmented to help reduce or eliminate inadvertent identification and/or removal of anatomical structures as recurring artifacts. In some embodiments, bony structure may have a spatial frequency along the length of an object that may be inadvertently identified as a recurring artifact (e.g., due to repetition of bony structures such as ribs). Accordingly, the image may be segmented into a soft tissue segmented image (which is further processed for identification and removal of recurring artifacts) and into a bony structure image (which is not further processed for identification and removal of recurring artifacts). Accordingly, anatomy that may appear as recurring (such as ribs) at frequencies of interest (e.g., frequency or range of frequencies corresponding to longitudinal collection periodicity) may be preserved in an image.

At 514, at least a portion of the reconstructed image (e.g., a soft tissue segmented image) is transformed into a spatial frequency domain, with the spatial frequency corresponding to a longitudinal direction. For example, a spatial domain image may be represented as p(x, y, z), and be transformed into a spatial frequency domain image corresponding to or being represented by a three-dimensional function S(x, y, ω), where ω is a frequency variable corresponding to a longitudinal frequency, or frequency in the z-direction.

At 516, a periodically recurring artifact (e.g., an artifact recurring periodically along a longitudinal direction or length of an image) is identified and removed based on a spatial frequency corresponding to a longitudinal collection periodicity to prove a corrected spatial frequency domain image. For example, the spatial frequency may be an inverse of the longitudinal collection periodicity, or be derived from the longitudinal collection periodicity. For example, a range of frequencies centered around or otherwise corresponding to the inverse of the longitudinal collection periodicity may be analyzed for peaks corresponding to recurring artifacts. As another example, an estimated or predetermined frequency may be adjusted based on acquired imaging information. In various embodiments, different substeps may be employed to identify and remove a periodically recurring artifact. For example, one or more of substeps 518-532 and/or one or more of substeps 534-544 may be employed in various embodiments.

At 518 noise is removed from the spatial frequency domain image. For example, recurring artifacts may not change sharply in the x-y plane, and noise may be removed utilizing a low-pass filter applied to S(x, y, ω) before analyzing S(x, y, ω) for recurring artifacts. Next, a thresholding analysis may be performed across at least one of a coronal plane or a sagittal plane to identify and remove recurring artifacts.

In the illustrated embodiment, at 520, a first line (or portion) of an image is set as a current line (or portion). For example, the first line (or portion) may be one of a series of lines (or portions) extending along a z-direction or longitudinal direction, with the lines (or portions) analyzed across at least one of an x-direction, y-direction, or as part of a 3 dimensional analysis (e.g., x and y). At 522, the value (e.g., intensity value) at a frequency (or frequencies) of interest (corresponding to a longitudinal collection periodicity) is determined for the current line. At 524, it is determined if the value for the current line satisfies or exceeds a threshold corresponding to a recurring artifact. If the threshold is not satisfied, it is determined that there is no recurring artifact for the current line, and the method 500 proceeds to 526, where it is determined if additional lines are present. If additional lines are present, the method proceeds to 528. At 528, the next line (or portion) is set as the current line (or portion) and the method 500 returns to 522.

If, however, it is determined at 524 that the value for the current line satisfied or exceeds the threshold, it is determined that a recurring artifact occurs for the current line, and information corresponding to the peak or value exceeding the threshold is removed from the spatial frequency domain image at 530. After removal of information corresponding to the peaks or portions exceeding the threshold, the method proceeds to 526, described above. If, at 526, it is determined that no further lines exist (e.g., all lines or portions have been examined), the method 500 proceeds to 532. At 532, undefined portions resulting from the removal of artifacts are filled in, for example based on interpolation using surrounding tissue. It may be noted that one or more of substeps 518-532 may be performed iteratively, for example using progressive thresholds. For instance a first threshold may be applied. After the first threshold is applied, it may be determined if artifacts remain above a predetermined desirable or acceptable level, and, if so, one or more steps may be repeated using a different threshold.

As another example of substeps that may be employed in various embodiments, at 534, a reference image is generated. The reference image, for example, may include bands (e.g., light and dark) at positions corresponding to a theoretical, expected, or determined periodicity of an imaging system, for example based on an increment, as one example, or a helical pitch, as another example, utilized during collection of the CT information at 502. At 536, a recurring artifact is detected, for example based on a frequency at which a peak value corresponding to a recurring artifact is detected. At 538, a standardized periodic structure or mask is generated, for example using the reference image from 534 adjusted to reflect actually identified artifacts from 536. At 540, the standardized periodic structure is applied to an image to generate a rectified image, and, at 542 artifacts are removed from the rectified image. At 544 undefined portions resulting from the removal of artifacts are filled in, for example based on interpolation using surrounding tissue. It may be noted that one or more of the substeps 534-544 may be performed as part of an iterative process, and/or one or more of the substeps may be performed first for one type of band (e.g., a dark band) and subsequently for one or more different types of band (e.g., a light band).

At 546, with a corrected spatial frequency image generated having at least one recurring artifact removed or reduce, an inverse transform is performed on the corrected spatial frequency image, for example to transform the corrected image from a frequency domain of image space (e.g., S(x, y, ω)) to a spatial domain of image space (e.g., p(x, y, z)), to provide a corrected image. At 548, the corrected image (in the depicted embodiment, a corrected soft tissue image) is combined with an additional portion of the original reconstructed image (in the illustrated embodiment, a bony structure image) to provide a combined image, which may be displayed at 550. It may be noted that axial images (as well as coronal and/or sagittal plane images) may be displayed, with the removed recurring artifacts no longer present in any of the views (axial, coronal, or sagittal).

Figure 8:
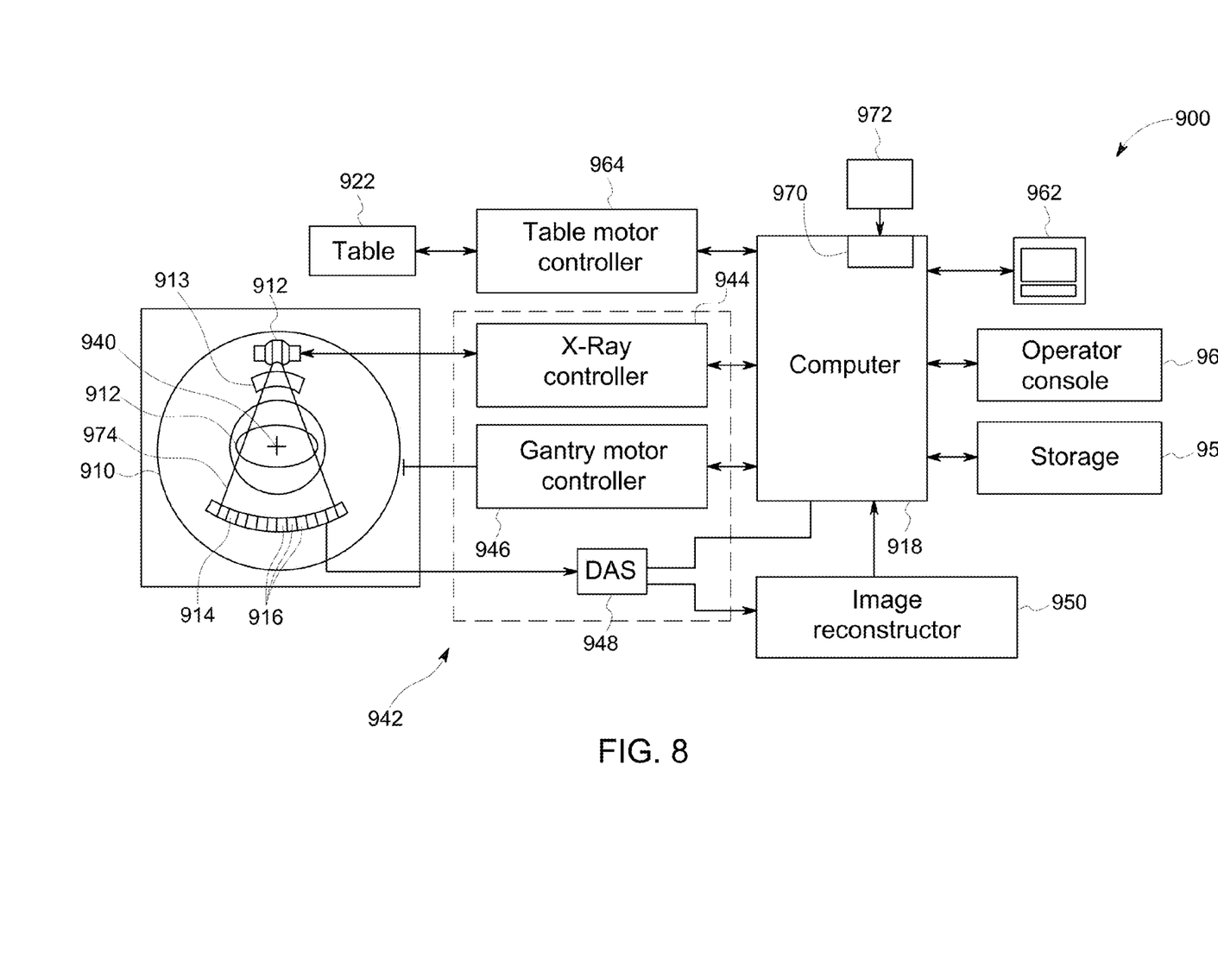
FIG. 8 is a schematic block diagram of an imaging system in accordance with various embodiments.

Various methods and/or systems (and/or aspects thereof) described herein may be implemented using a medical imaging system. For example, FIG. 8 is a block schematic diagram of an exemplary CT imaging system 900 that may be utilized to implement various embodiments discussed herein. Although the CT imaging system 900 is illustrated as a standalone imaging system, it should be noted that the CT imaging system 900 may form part of a multi-modality imaging system in some embodiments. For example, the multi-modality imaging system may include the CT imaging system 900 and a positron emission tomography (PET) imaging system, or a single photon emission computed tomography (SPECT) imaging system. It should also be understood that other imaging systems capable of performing the functions described herein are contemplated as being used.

The CT imaging system 900 includes a gantry 910 that has the X-ray source 912 that projects a beam of X-rays toward the detector array 914 on the opposite side of the gantry 910. A source collimator 913 and a bowtie filter are provided proximate the X-ray source 912. In various embodiments, the source collimator 913 may be configured to provide wide collimation as discussed herein. The detector array 914 includes a plurality of detector elements 916 that are arranged in rows and channels that together sense the projected X-rays that pass through a subject 917. The imaging system 900 also includes a computer 918 that receives the projection data from the detector array 914 and processes the projection data to reconstruct an image of the subject 917. The computer 918, for example, may include one or more aspects of the processing unit 120, or be operably coupled to one or more aspects of the processing unit 120. In operation, operator supplied commands and parameters are used by the computer 918 to provide control signals and information to reposition a motorized table 922. More specifically, the motorized table 922 is utilized to move the subject 917 into and out of the gantry 910. Particularly, the table 922 moves at least a portion of the subject 917 through a gantry opening (not shown) that extends through the gantry 910. Further, the table 922 may be used to move the subject 917 vertically within the bore of the gantry 910.

The depicted detector array 914 includes a plurality of detector elements 916. Each detector element 916 produces an electrical signal, or output, that represents the intensity of an impinging X-ray beam and hence allows estimation of the attenuation of the beam as it passes through the subject 917. During a scan to acquire the X-ray projection data, the gantry 910 and the components mounted thereon rotate about a center of rotation 940. FIG. 8 shows only a single row of detector elements 916 (i.e., a detector row). However, the multislice detector array 914 includes a plurality of parallel detector rows of detector elements 916 such that projection data corresponding to a plurality of slices can be acquired simultaneously during a scan.

Rotation of the gantry 910 and the operation of the X-ray source 912 are governed by a control mechanism 942. The control mechanism 942 includes an X-ray controller 944 that provides power and timing signals to the X-ray source 912 and a gantry motor controller 946 that controls the rotational speed and position of the gantry 910. A data acquisition system (DAS) 948 in the control mechanism 942 samples analog data from detector elements 916 and converts the data to digital signals for subsequent processing. An image reconstructor 950 receives the sampled and digitized X-ray data from the DAS 948 and performs high-speed image reconstruction. The reconstructed images are input to the computer 918 that stores the image in a storage device 952. The computer 918 may also receive commands and scanning parameters from an operator via a console 960 that has a keyboard. An associated visual display unit 962 allows the operator to observe the reconstructed image and other data from computer. It may be noted that one or more of the computer 918, controllers, or the like may be incorporated as part of a processing unit such as the processing unit 120 discussed herein.

The operator supplied commands and parameters are used by the computer 918 to provide control signals and information to the DAS 948, the X-ray controller 944 and the gantry motor controller 946. In addition, the computer 918 operates a table motor controller 964 that controls the motorized table 922 to position the subject 917 in the gantry 910. Particularly, the table 922 moves at least a portion of the subject 917 through the gantry opening.

In various embodiments, the computer 918 includes a device 970, for example, a CD-ROM drive, DVD drive, magnetic optical disk (MOD) device, or any other digital device including a network connecting device such as an Ethernet device for reading instructions and/or data from a tangible non-transitory computer-readable medium 972, that excludes signals, such as a CD-ROM, a DVD or another digital source such as a network or the Internet, as well as yet to be developed digital means. In another embodiment, the computer 918 executes instructions stored in firmware (not shown). The computer 918 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

In the exemplary embodiment, the X-ray source 912 and the detector array 914 are rotated with the gantry 910 within the imaging plane and around the subject 917 to be imaged such that the angle at which an X-ray beam 974 intersects the subject 917 constantly changes. A group of X-ray attenuation measurements, i.e., projection data, from the detector array 914 at one gantry angle is referred to as a "view" or "projection." A "scan" of the subject 917 comprises a set of views made at different gantry angles, or view angles, during one or more revolutions of the X-ray source 912 and the detector array 914. In a CT scan, the projection data is processed to reconstruct an image that corresponds to a three-dimensional volume taken of the subject 917. It may be noted that, in some embodiments, an image may be reconstructed using less than a full revolution of data. For example, with a multi-source system, substantially less than a full rotation may be utilized. Thus, in some embodiments, a scan (or slab) corresponding to a 360 degree view may be obtained using less than a complete revolution.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a processing unit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. An imaging system comprising:
a computed tomography (CT) acquisition unit comprising an X-ray source and a CT detector configured to collect CT imaging data of an object to be imaged, the object including an acquisition volume comprising a cross-section extending along a longitudinal direction, the X-ray source and CT detector configured to be rotated relative to the object to be imaged and to collect a series of projections of the object as the X-ray source and CT detector rotate relative the object to be imaged, the CT acquisition unit further configured to translate axially relative to the object to be imaged along the longitudinal direction to collect the CT imaging data at plural imaging locations along the longitudinal direction defining a longitudinal collection periodicity; and
at least one processor operably coupled to the CT acquisition unit, the at least one processor configured to:
reconstruct an image using the CT imaging information;

extract spatial frequency information from at least a portion of the image, wherein the spatial frequency is defined along the longitudinal direction; and remove a periodically recurring artifact from the at least a portion of the image based on a spatial frequency corresponding to the longitudinal collection periodicity to provide a corrected image.

2. The imaging system of claim 1, wherein the at least one processor is configured to:

transform the at least a portion of the image to a spatial frequency domain to provide a spatial frequency domain image;

remove the periodically recurring artifact from the spatial frequency domain image to provide a corrected spatial frequency domain image; and perform an inverse transform on the corrected spatial frequency domain image to provide the corrected image.

3. The imaging system of claim 1, wherein the at least one processor is configured to remove the periodically recurring artifact via a thresholding analysis performed across at least one of a coronal plane or a sagittal plane.

4. The imaging system of claim 1, wherein the at least one processor is configured to segment the image to provide a bony structure segmented image and a soft tissue segmented image, wherein the at least a portion of the image transformed to the spatial frequency domain includes the soft tissue segmented image but not the bony structure segmented image.

5. The imaging system of claim 1, wherein the CT imaging information is collected during a helical acquisition, wherein the periodicity is defined as T=D×K, wherein T is the periodicity, D is the detector coverage along the longitudinal direction at an iso-center of an acquisition unit collecting the CT information, and K is the helical pitch.

6. The imaging system of claim 1, wherein the CT imaging information is collected during a step-and-shoot acquisition, wherein the periodicity is defined as the increment between steps along the longitudinal direction.

7. The imaging system of claim 1, wherein the at least one processor is configured to identify the periodically recurring artifact, generate a standardized periodic structure corresponding to the identified periodically recurring artifact to provide a rectified image, and remove the periodically recurring artifact from the rectified image to provide the corrected spatial frequency domain image.

8. The imaging system of claim 1, wherein the at least one processor is configured to adjust a threshold of an artifact correction based on at least one of a location of an artifact relative to an iso-center of the imaging system or a slope of a bowtie filter.

9. A method comprising:

acquiring computed tomography (CT) imaging information of an acquisition volume comprising a cross-section extending along a longitudinal direction, wherein the CT imaging information is collected at plural imaging locations along the longitudinal direction defining a longitudinal collection periodicity;

reconstructing an image using the CT imaging information;

extracting spatial frequency information from at least a portion of the image, wherein the spatial frequency is defined along the longitudinal direction; and removing a periodically recurring artifact from the at least a portion of the image based on a spatial frequency corresponding to the longitudinal collection periodicity to provide a corrected image.

10. The method of claim 9, wherein extracting the spatial frequency information includes transforming the at least a portion of the image to a spatial frequency domain to provide a spatial frequency domain image, wherein removing the periodically recurring artifact comprises removing the periodically recurring artifact from the spatial frequency domain image to provide a corrected spatial frequency domain image, the method further comprising performing an inverse transform on the corrected spatial frequency domain image to provide the corrected image.

11. The method of claim 9, wherein the periodically recurring artifact is removed via a thresholding analysis performed across at least one of a coronal plane or a sagittal plane.

12. The method of claim 9, further comprising segmenting the image to provide a bony structure segmented image and a soft tissue segmented image, wherein the at least a portion of the image transformed to the spatial frequency domain includes the soft tissue segmented image but not the bony structure segmented image.

13. The method of claim 9, wherein the CT imaging information is collected during a helical acquisition, wherein the periodicity is defined as T=D×K, wherein T is the periodicity, D is the detector coverage along the longitudinal direction at an iso-center of an acquisition unit collecting the CT information, and K is the helical pitch.

14. The method of claim 9, wherein the CT imaging information is collected during a step-and-shoot acquisition, wherein the periodicity is defined as the increment between steps along the longitudinal direction.

15. The method of claim 9, wherein removing the periodically recurring artifact comprises identifying the periodically recurring artifact, generating a standardized periodic structure corresponding to the identified periodically recurring artifact to provide a rectified image, and removing the periodically recurring artifact from the rectified image to provide the corrected spatial frequency domain image.

16. A tangible and non-transitory computer readable medium comprising one or more computer software modules configured to direct one or more processors to:

acquire computed tomography (CT) imaging information of an acquisition volume comprising a cross-section extending along a longitudinal direction, wherein the CT imaging information is collected at plural imaging locations along the longitudinal direction defining a longitudinal collection periodicity;

reconstruct an image using the CT imaging information;

extract spatial frequency information from at least a portion of the image, wherein the spatial frequency is defined along the longitudinal direction; and remove a periodically recurring artifact from the at least a portion of the image based on a spatial frequency corresponding to the longitudinal collection periodicity to provide a corrected image.

17. The tangible and non-transitory computer readable medium of claim 16, wherein the one or more computer software modules are further configured to direct the one or more processors to:

transform the at least a portion of the image to a spatial frequency domain to provide a spatial frequency domain image;

remove the periodically recurring artifact from the spatial frequency domain image to provide a corrected spatial frequency domain image; and perform an inverse transform on the corrected spatial frequency domain image to provide the corrected image.

18. The tangible and non-transitory computer readable medium of claim 17, wherein the one or more computer software modules are further configured to direct the one or more processors to segment the image to provide a bony structure segmented image and a soft tissue segmented image, wherein the at least a portion of the image transformed to the spatial frequency domain includes the soft tissue segmented image but not the bony structure segmented image.

19. The tangible and non-transitory computer readable medium of claim 17, wherein the CT imaging information is collected during a helical acquisition, wherein the periodicity is defined as $T=D \times K$, wherein T is the periodicity, D is the detector coverage along the longitudinal direction at an iso-center of an acquisition unit collecting the CT information, and K is the helical pitch.

20. The tangible and non-transitory computer readable medium of claim 17, wherein the CT imaging information is collected during a step-and-shoot acquisition, wherein the periodicity is defined as the increment between steps along the longitudinal direction.

\* \* \* \* \*